US009801549B2

(12) United States Patent
Panitz et al.

(10) Patent No.: US 9,801,549 B2
(45) Date of Patent: Oct. 31, 2017

(54) APPARATUS FOR FINDING A FUNCTIONAL TISSUE AREA IN A TISSUE REGION

(71) Applicants: Carl Zeiss Meditec AG, Jena (DE); Technische Universitaet Dresden Institut fuer Biomedizinische Technik, Dresden (DE); Technische Universitaet Dresden Klinik und Poliklinik fuer Neurochirurgie, Dresden (DE)

(72) Inventors: Gerald Panitz, Ellwangen (DE); Christoph Hauger, Aalen (DE); Marco Wilzbach, Stuttgart (DE); Roland Guckler, Ulm (DE); Tobias Meyer, Dresden (DE); Martin Oelschlaegel, Dresden (DE); Ute Morgenstern, Dresden (DE); Stephan B. Sobottka, Dresden (DE); Gabriele Schackert, Dresden (DE)

(73) Assignees: Carl Zeiss Meditec AG, Jena (DE); Technische Universitaet Dresden Institut fuer Biomedizinische Technik, Dresden (DE); Technische Universitaet Dresden Klinik und Poliklinik fuer Neurochirurgie, Dresden (DE)

( * ) Notice: Subject to any disclaimer, the term of this patent is extended or adjusted under 35 U.S.C. 154(b) by 185 days.

(21) Appl. No.: 14/686,252

(22) Filed: Apr. 14, 2015

(65) Prior Publication Data

US 2015/0289765 A1 Oct. 15, 2015

(30) Foreign Application Priority Data

Apr. 14, 2014 (DE) ........................ 10 2014 005 407

(51) Int. Cl.
*A61B 5/00* (2006.01)
*A61B 5/026* (2006.01)
(Continued)

(52) U.S. Cl.
CPC .......... *A61B 5/0075* (2013.01); *A61B 5/0261* (2013.01); *A61B 5/14553* (2013.01);
(Continued)

(58) Field of Classification Search
CPC . A61B 5/0075; A61B 5/0261; A61B 5/14553; A61B 5/742; A61B 90/20
See application file for complete search history.

(56) References Cited

U.S. PATENT DOCUMENTS

| 5,215,095 A | 6/1993 | Macvicar et al. |
| 6,196,226 B1 | 3/2001 | Hochman et al. |
(Continued)

OTHER PUBLICATIONS

English translation and the Office action of the German Patent Office dated Nov. 18, 2014 in German patent application 10 2014 005 407.1 on which the claim of priority is based.

*Primary Examiner* — Scott Getzow
(74) *Attorney, Agent, or Firm* — Walter Ottesen, P.A.

(57) ABSTRACT

The invention is directed to an apparatus for finding a functional tissue area in a tissue region. The apparatus has a measurement illuminating device suitable for emitting measurement illumination to the tissue region and a camera which can capture light reflected by the tissue region. The camera has a green channel and/or a blue channel wherein there is a change in an optical property of the light reflected by the tissue region during the stimulation thereof which is undertaken at least intermittently. An evaluation unit captures the change in the optical property only by a signal of the green channel and/or of the blue channel of the camera. A display unit can display an output signal of the evaluation unit for the functional tissue area in the tissue region.

9 Claims, 3 Drawing Sheets

(51) Int. Cl.
*A61B 5/1455* (2006.01)
*A61B 90/20* (2016.01)

(52) U.S. Cl.
CPC .............. *A61B 5/742* (2013.01); *A61B 90/20* (2016.02); *A61B 2505/05* (2013.01); *A61B 2576/02* (2013.01)

(56) References Cited

U.S. PATENT DOCUMENTS

2003/0158470 A1* 8/2003 Wolters .................. A61B 1/043 600/317
2010/0254586 A1 10/2010 Fanenbruck
2010/0262017 A1* 10/2010 Frangioni ............ A61B 1/0005 600/476
2014/0378810 A1* 12/2014 Davis ........................ G06T 5/40 600/407

\* cited by examiner

US 9,801,549 B2

APPARATUS FOR FINDING A FUNCTIONAL TISSUE AREA IN A TISSUE REGION

CROSS REFERENCE TO RELATED APPLICATION

This application claims priority of German patent application no. 10 2014 005 407.1, filed Apr. 14, 2014, the entire content of which is incorporated herein by reference.

FIELD OF THE INVENTION

The present invention relates to an apparatus for finding a functional tissue area in a tissue region, especially in a brain tissue region. The invention further relates to a method for finding a functional tissue area in a tissue region and a surgical microscope having an apparatus referred to above.

BACKGROUND OF THE INVENTION

In the case of tumor surgery in the brain with a tumor in the vicinity of eloquent brain areas, that is, functional brain areas, such as, for example, in the vicinity of the motor cortex, in the vicinity of the sensorimotor centers or in the vicinity of the speech center, a surgeon is presented with the conflicting goals of, on the one hand, radically removing the tumor and, on the other hand, removing as little tissue required for healthy brain function as possible. Therefore, finding the functional brain areas as precisely as possible is of great importance.

One option for finding functional brain areas consists of detecting these areas by electrophysiological means, for example, by electrical stimulation of specific muscles and the subsequent potential measurement on the brain surface by applied electrodes. A disadvantage consists of the electrode size limiting the resolution when finding the functional tissue areas. Furthermore, it is disadvantageous, as a matter of principle, that the tissue area comes into contact with an article that is foreign to tissue, as is represented by an electrode, and so injuries can result therefrom.

U.S. Pat. No. 6,196,226 B1 or U.S. Pat. No. 5,215,095 proposes to represent functional brain areas by an optical image. Methods described in these patents comprise the tissue region being recorded during a stimulation that leads to a change in the physiological properties of the functional areas. The change in the physiological properties in turn leads to a change in the optical properties of reflected light. Therefore, a difference is formed between a stimulation image recorded during the stimulation and a comparison image recorded without stimulation in order to depict the functional areas and the functional areas are found on the basis of the difference.

A disadvantage of these methods lies in the fact that they are relatively difficult to perform since the changes connected with the functional stimulations have a weak intensity in the reflected light. Furthermore, use is made of a relatively expensive monochrome camera (black/white camera) with a high grayscale resolution and a relatively long integration time. Hence, finding functional tissue areas is relatively time intensive and expensive. Moreover, this means a relatively long time of surgery, which is unwanted for a patient as a matter of principle.

SUMMARY OF THE INVENTION

It is an object of the invention to develop and provide an apparatus for finding a functional tissue area in a tissue region. The apparatus is cost-effective and enables contrast-rich imaging of the functional tissue area in a short period of time. It is furthermore an object of the invention to develop and provide a method for finding a functional tissue area in a tissue region. It is furthermore an object of the invention to develop a surgical microscope comprising such an apparatus.

The apparatus according to the invention for finding a functional tissue area in a tissue region includes:
- a measurement illuminating device suitable for emitting measurement illumination to the tissue region;
- a camera which can acquire light reflected by the tissue region, the camera having a green channel and/or a blue channel, wherein there is a change in at least one optical property of the light reflected by the tissue region during the stimulation of the tissue region which is undertaken at least intermittently;
- an evaluation unit, which acquires the change in the at least one optical property exclusively by a signal of the green channel and/or of the blue channel of the camera; and,
- a display unit for displaying an output signal of the evaluation unit for the functional tissue area in the tissue region.

The inventors have identified that an expensive monochrome camera with an associated color filter is not mandatory for being able to find a functional tissue area in a tissue region. Rather, it is sufficient to make use of a color image camera with a green channel and/or a blue channel with a color sensor for a green range and a blue range. After an intermittent stimulation of a tissue region was performed, it is possible to register a sufficient change in at least one optical property of the light reflected by the tissue region in the green range, that is, in a wavelength range between approximately 470 nm and 600 nm, or in the blue range, that is, in the wavelength range between approximately 400 nm and 520 nm. If the light reflected by the stimulated tissue region is acquired in the relatively broad wavelength range of between 470 nm and 600 nm (green range) or between 400 nm and 520 nm (blue range), this change in the at least one optical property can be fed to an evaluation unit. According to the invention, the output signal of such an evaluation unit can be fed to a downstream display unit, by means of which a functional tissue area in the tissue region is displayable.

It is possible to obtain a high measurement sensitivity by virtue of the evaluation unit acquiring the change in the at least one optical property only by means of the signal of the green channel and/or of the blue channel. Signals from a red channel are therefore masked deliberately.

Preferably, the at least one optical property is the intensity or wavelength of the reflected light. A stimulation of the tissue region leads to neuronal activity and therefore to an increased oxygen consumption. This results in an expansion of arterioles and therefore to higher blood flow with a higher blood volume in the corresponding tissue region. In addition to such a change in the blood volume, there moreover is a change in the oxygen saturation of the hemoglobin in the blood. The increased oxygen requirement brings about an increase in the deoxygenated hemoglobin and oxygenated hemoglobin. If such a tissue region is illuminated, this leads to a change in the absorption of the reflected light. Thus, this is therefore accompanied by a change in the intensity of the reflected light, wherein the change in intensity can be acquired by a camera. If the camera acquires such a change in the intensity in a wavelength range between 400 nm and 520 nm and/or in a wavelength range between 470 nm and 600 nm, this is enough to identify a functional tissue area in the tissue region.

Preferably, the change in the at least one optical property is pulsed. This can be achieved by virtue of the stimulation being brought about in a pulsed manner. Thus, there is a periodic change between the cortical stimulation and no stimulation, which is easily implementable by means of process control.

In accordance with a preferred development of the invention, the measurement illuminating device is configured to emit pulsed measurement illumination. When a measurement illumination is not switched on, the acquired signal from the camera means a value which was induced by stray light or ambient light. This value can be subtracted from the measurement results obtained when the measurement illumination is switched on.

An object of the invention is achieved by a method for finding or locating a functional tissue area in a tissue region. The method includes the steps of:
  illuminating the tissue region with a measurement illuminating device;
  at least intermittent stimulating of the tissue region to bring about a change of at least one optical property of the light reflected by the tissue region;
  acquiring the change in the at least one optical property by means of an evaluation unit only by means of a signal of a green channel and/or a blue channel of a camera, which has the green channel and/or the blue channel; and,
  outputting an output signal of the evaluation unit to a display unit.

Using this method, a contrast-rich image of a functional tissue area in a tissue region can be obtained in a cost-effective and quick manner, and with little complexity.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
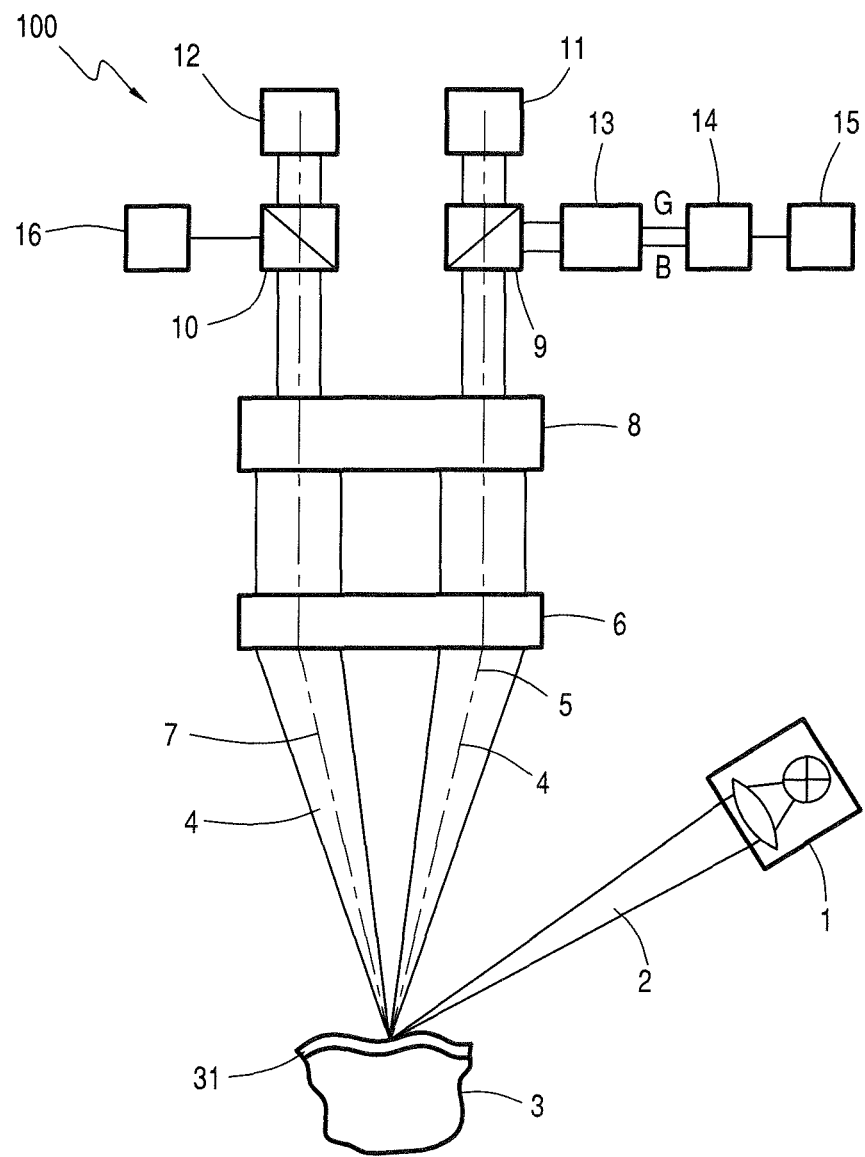
FIG. 1 shows a schematic of the apparatus according to the invention in accordance with a first embodiment.

FIG. 1 schematically depicts an apparatus 100 according to the invention in accordance with a first embodiment for finding a functional tissue area in a tissue region 3. The apparatus 100 has a measurement illuminating device 1 which may have a xenon lamp or halogen lamp. The measurement illuminating device 1 transmits white light 2 to a tissue area in a tissue region 3 which, for example, has a blood path 31. The light 4 reflected by the blood path 31 reaches an objective 6 in a first beam path 5 and, from there, it reaches a magnification changer 8. From there, the light reaches a first beam splitter 9, from where the light reaches an eyepiece 11 and a camera 13. The camera 13 has a green channel G and a blue channel B, which are both coupled to an evaluation unit 14. When the tissue area in the tissue region 3 is stimulated in such a way that there is a change in the concentration of oxygenated and deoxygenated hemoglobin, this brings about a change in the absorption of the reflected light 4, which can be captured as a change in the intensity by the green channel and/or blue channel of the camera. In the present embodiment of the invention, this change in the intensity is acquired by the evaluation unit 14 and subsequently displayed at a display unit 15.

The apparatus 100 furthermore has a second beam path 7, in which the reflected light 4 is supplied to the objective 6 and, from there, it reaches the magnification changer 8. Along this second beam path 7, the light can subsequently reach a second beam splitter 10, from where the light can reach, firstly, a second eyepiece 12 and, secondly, an optical component 16. The optical component 16 can be an additional camera or display unit, by means of which information is coupled into the second beam path. Consequently, the second beam splitter 10 can serve either to couple additional information into the beam path or to feed the reflected light 4 to an optical component 16.

Figure 2:
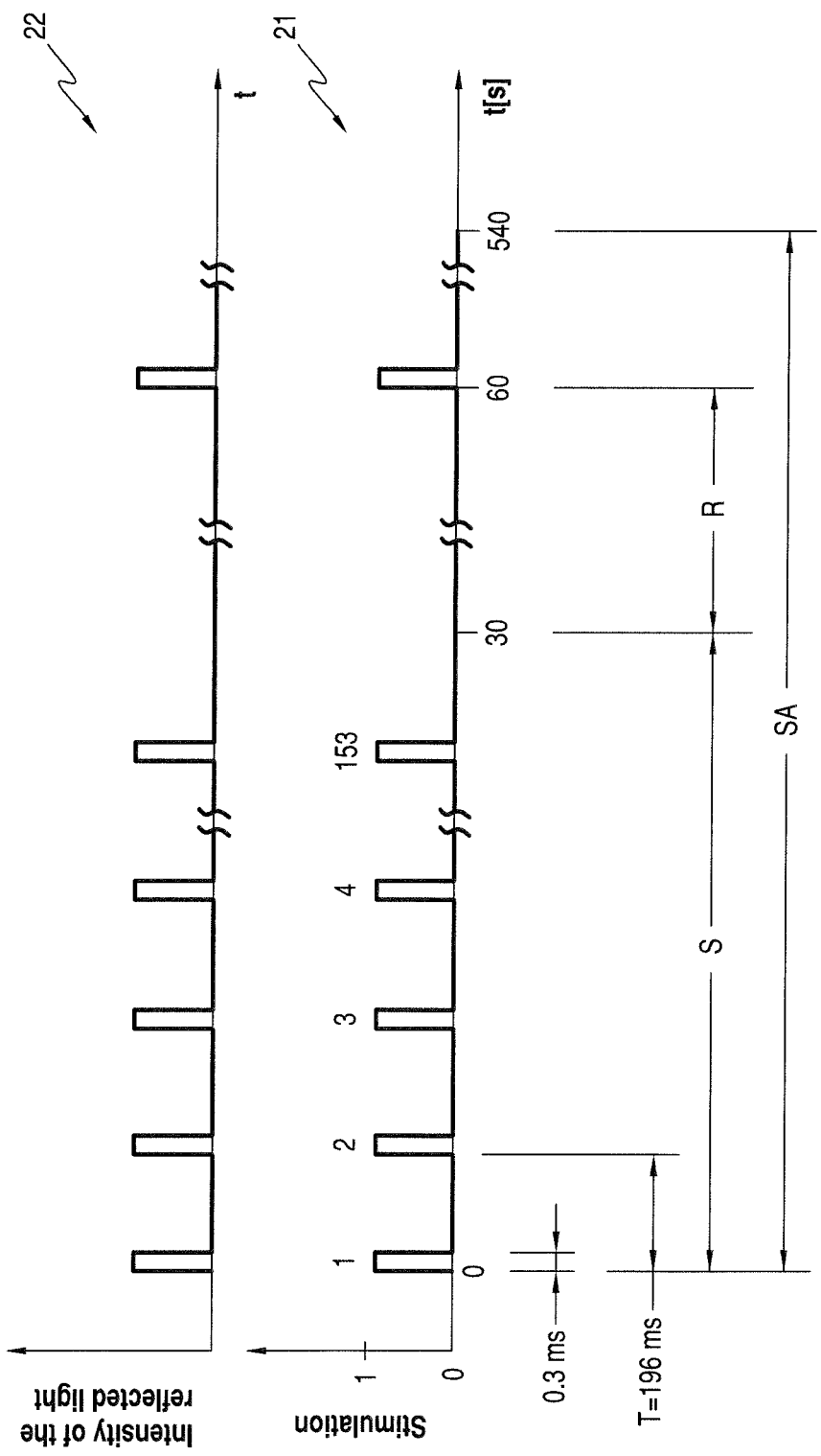
FIG. 2 shows a schematic of a stimulation pattern for stimulating a tissue region to be found with the apparatus according to the invention; and, FIG. 3 shows a diagram which shows the spectral sensitivity of a red channel, green channel and blue channel of a color camera and an absorption coefficient of oxygenated hemoglobin and deoxygenated hemoglobin.

FIG. 2 depicts a schematic of a stimulation procedure. The diagram 21 shows a sequence of stimulation stimuli, which, for example, are each applied for a time duration of 0.3 ms. By way of example, this can be achieved by a flash of light. After such a first flash of light, there is a relatively long pause, and so, after a period of 196 ms has passed, this is followed by a second flash of light with a time duration of 0.3 ms. This pattern of flash of light and pause repeats 153 times, such that a stimulation phase S is completed after 30 seconds. This is followed by a rest phase R with a duration of 30 seconds, during which there are no flashes of light, that is, no stimulation of a tissue area in a tissue region. This pattern of stimulation phase S and rest phase R is repeated nine times and so the stimulation procedure SA is completed after 540 seconds.

Diagram 22 in FIG. 2 shows the reactions which are determinable in the functional tissue area to be examined on account of the flashes of light. The reaction consists of a change in at least one optical property of the light reflected by the tissue region. In the present diagram 22, this is the intensity of the reflected light. It is clear that the reaction in the functional tissue area follows the stimulation stimulus with virtually no delay. Consequently, there are a sufficient number of reactions in the functional tissue area in the tissue region to be examined at the end of the whole stimulation procedure. A functional tissue area in a tissue region can be easily identified by comparing recordings in which a stimulation took place with recordings in which there was no stimulation. It is therefore possible to make a statement about the state of the tissue region if, in the process, a different cortical perfusion is determined in the tissue area to be examined. This allows for a distinction to be made between a healthy tissue region and a pathological tissue region which, for example, has been changed by a tumor.

Figure 3:
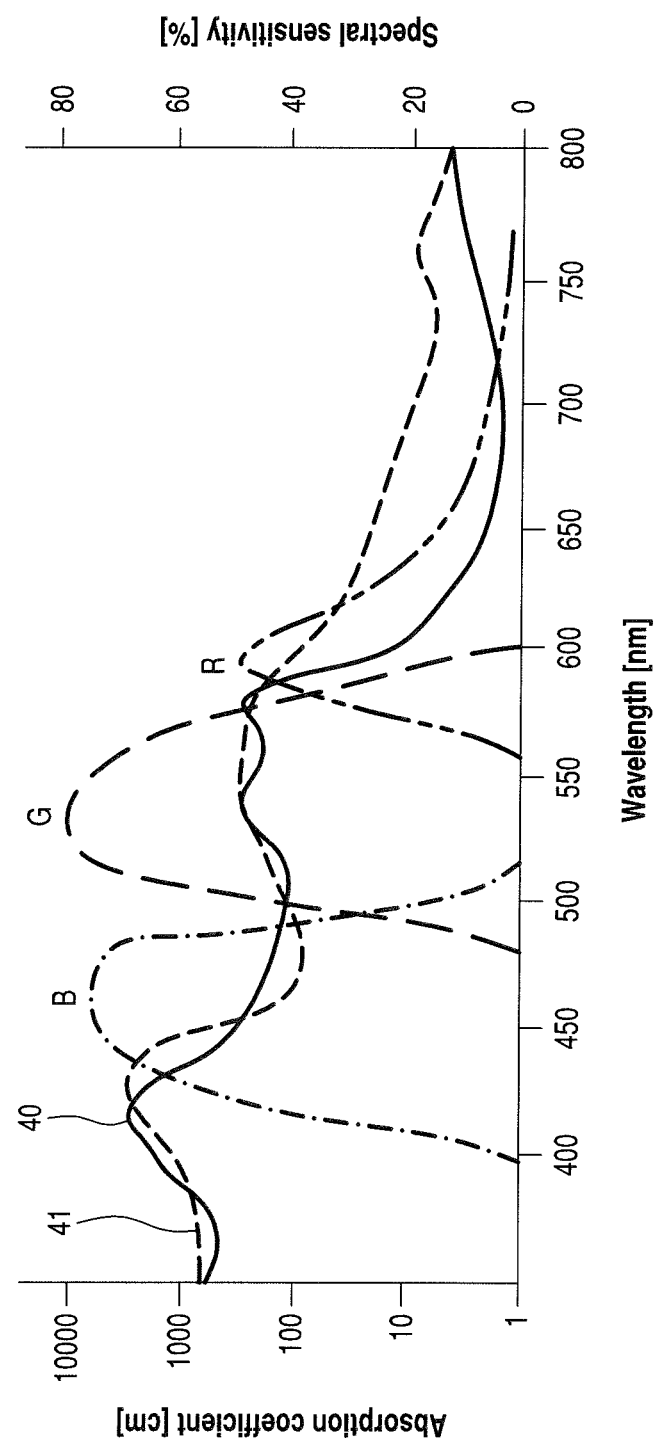

FIG. 3 depicts a diagram which shows the spectral sensitivity of a red channel, blue channel and green channel of a color camera as a function of the wavelength. The blue channel—see curve "B"—has a sensitivity in the range from 400 nm to approximately 520 nm, with the green channel—see curve "G"—having a sensitivity approximately in the range from 470 nm to 600 nm. The red channel covers a wavelength range from approximately 560 nm to 760 nm. Additionally, FIG. 3 depicts an absorption coefficient for oxygenated hemoglobin and deoxygenated hemoglobin as a function of the wavelength. The absorption coefficient for oxygenated hemoglobin—see the curve profile with respect to reference numeral 40—lies relatively close to the curve profile of deoxygenated hemoglobin—see curve profile 41—in the region of the blue channel and the green channel of a color camera. In the range between 400 nm and 450 nm, the absorption coefficient lies in the range from 200 to 2000 $cm^{-1}$. In the range from 450 nm to approximately 580 nm, the absorption coefficient for oxygenated and deoxygenated hemoglobin lies between approximately 90 and 200 $cm^{-1}$. Above approximately 570 nm, the absorption coefficient for oxygenated hemoglobin greatly reduces to only approximately 2 $cm^{-1}$, with the absorption coefficient for deoxygenated hemoglobin sinking to approximately 5 $cm^{-1}$. The profile of the curves 40 and 41 clearly shows that there is a relatively high absorption coefficient for both oxygenated and deoxygenated hemoglobin in the case of a wavelength of less than 570 nm, and so a significant change in the absorption, and hence in the intensity, can be acquired in the case of the stimulation of a functional tissue area in a tissue region to be examined by means of a green channel and a blue channel.

The inventors have identified that functional tissue areas are easily identifiable in a tissue region by means of a green channel and/or blue channel, even in this relatively large wavelength range from 440 nm to approximately 570 nm.

It is understood that the foregoing description is that of the preferred embodiments of the invention and that various changes and modifications may be made thereto without departing from the spirit and scope of the invention as defined in the appended claims.

What is claimed is:

1. An apparatus for finding a functional tissue area in a tissue region, the apparatus comprising:
   a measurement illuminating device configured to emit a measurement illumination on to the tissue region;
   a camera for capturing light reflected from the tissue region;
   said camera being configured to have at least one of a green channel and a blue channel wherein there is a change in at least one optical property of the light reflected by the tissue region during stimulation of the tissue region undertaken at least intermittently;
   said camera being further configured to emit a camera signal exclusively of at least one of said green channel and said blue channel;
   an evaluation unit for detecting the change in the at least one optical property only via said camera signal and supplying an output signal; and,
   a display unit for displaying said output signal of said evaluation unit for the functional tissue area of the tissue region.

2. The apparatus of claim 1, wherein said at least one optical property is an intensity or a wavelength of the reflected light.

3. The apparatus of claim 1, wherein the change of the at least one optical property is pulsed.

4. The apparatus of claim 1, wherein said measurement illuminating device is configured to emit a pulsed measurement illumination.

5. A method of finding a functional tissue area in a tissue region, the method comprising the steps of:
   providing a camera exclusively having a green channel and/or a blue channel;
   illuminating the tissue region with a measurement illuminating device;
   at least intermittently stimulating the tissue region to cause a change of at least one optical property of the light reflected by the tissue region;
   capturing the change of the at least one optical property by an evaluation unit only via a signal of the green channel and/or blue channel of the camera; and,
   displaying an output signal of the evaluation unit on a display unit.

6. A surgical microscope comprising:
   an apparatus for finding a functional tissue area in a tissue region, the apparatus including:
   a measurement illuminating device configured to emit a measurement illumination on to the tissue region;
   a camera for capturing light reflected from the tissue region;
   said camera being configured to have at least one of a green channel and a blue channel wherein there is a change in at least one optical property of the light reflected by the tissue region during stimulation of the tissue region undertaken at least intermittently;
   said camera being further configured to emit a camera signal exclusively of at least one of said green channel and said blue channel;
   an evaluation unit for detecting the change in the at least one optical property only via said camera signal and supplying an output signal; and,
   a display unit for displaying said output signal of said evaluation unit for the functional tissue area of the tissue region.

7. The surgical microscope of claim 6, wherein said at least one optical property is an intensity or a wavelength of the reflected light.

8. The surgical microscope of claim 6, wherein the change of the at least one optical property is pulsed.

9. The surgical microscope of claim 6, wherein said measurement illuminating device is configured to emit a pulsed measurement illumination.

\* \* \* \* \*